United States Patent [19]

Ek et al.

[11] Patent Number: 5,571,131
[45] Date of Patent: Nov. 5, 1996

[54] BACK BITING PUNCH

[75] Inventors: Steven Ek, Bolton, Mass.; David M. Auerbach, Encino, Calif.

[73] Assignee: Smith & Nephew Endoscopy, Inc., Andover, Mass.

[21] Appl. No.: 484,984

[22] Filed: Jun. 7, 1995

[51] Int. Cl.$^6$ .................................. A61B 17/14
[52] U.S. Cl. ..................... 606/184; 606/167; 606/170; 606/205; 606/207; 128/751
[58] Field of Search ................... 606/167, 170, 606/159, 180, 174, 176, 205, 207, 184; 128/751, 753; 604/22

[56] References Cited

U.S. PATENT DOCUMENTS

| | | | |
|---|---|---|---|
| 5,112,346 | 5/1992 | Hiltebrandt et al. | 606/170 |
| 5,219,357 | 6/1993 | Honkanen et al. | 606/174 |
| 5,286,255 | 2/1994 | Weber | 604/22 |
| 5,327,896 | 7/1994 | Schmieding | 128/753 |
| 5,352,235 | 10/1994 | Koros et al. | 606/170 |
| 5,389,104 | 2/1995 | Hahnen et al. | 606/174 |
| 5,443,475 | 8/1995 | Auerbach et al. | 606/170 |

FOREIGN PATENT DOCUMENTS

WO92/08415  5/1992  WIPO ............. A61B 17/32

OTHER PUBLICATIONS

Brochure, Acufex®, "Stingray The Anterior Horn Punch From Acufex.", 1994.
Brochure, Linvatec, "Introducing the Shut® Mantis™ Retrograde Forceps" 1993 Linvatech Corp.
Brochure, Acufex® Product Catalog, "The quality you expect. The Refinements you demand," 1994.

*Primary Examiner*—Michael Powell Buiz
*Assistant Examiner*—Kevin Truong
*Attorney, Agent, or Firm*—Fish & Richardson P.C.

[57] ABSTRACT

A surgical cutting instrument for cutting body tissue has an axially elongated support shaft which supports, at a distal end thereof, a back biting assembly. The back biting assembly has a ring-shaped jaw member pivotally supported by the support shaft at a distal end thereof for rearward pivotal movement toward and away from a closed cutting position. A fixed cutting block member, supported by the support shaft at a position proximally of the pivot axis of the ring-shaped member is aligned with and cuttingly engages the ring-shaped member to cut or punch any tissue within the opening of the pivotal jaw member. The fixed cutter member can have a serrated, parallel rib surface facing the moveable jaw member, with at least one serration being taller than the others for blocking the entry of tissue or other foreign objects into the space wherein the pivotable member rotates thereby to prevent blocking of that rotation by such foreign objects. The leading edge of the pivotable member is fashioned with a reduced thickness to better slip beneath and engage tissue such as, for example, meniscus tissue.

6 Claims, 5 Drawing Sheets

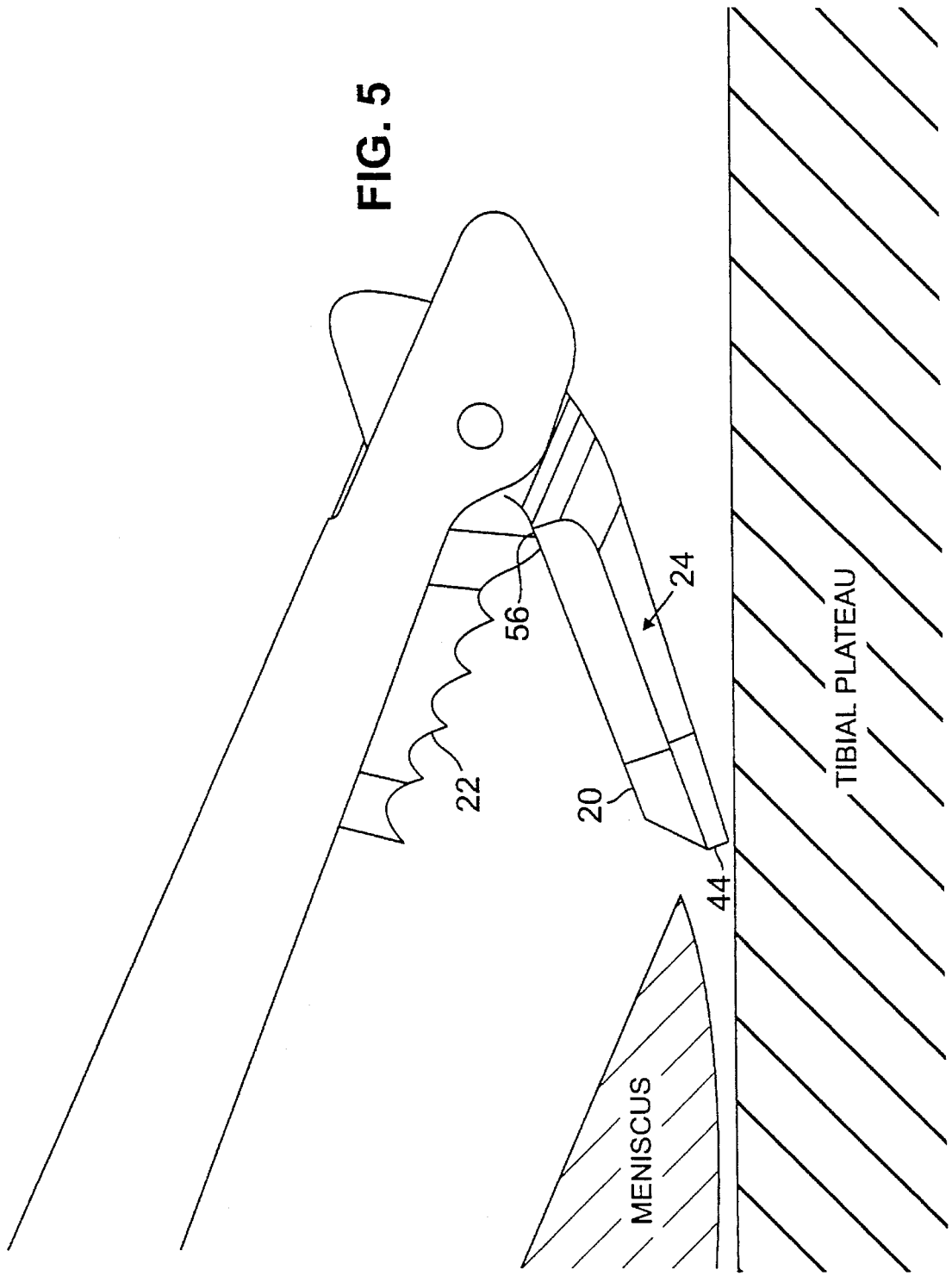

5,571,131

BACK BITING PUNCH

The invention relates generally to surgical instruments, and more particularly, to a backbiting surgical instrument for cutting or punching tissue such as, for example meniscus or cartilage at or near a joint of the body, such as the wrist or knee.

BACKGROUND OF THE INVENTION

It is well known in modern arthroscopic surgery that certain tissue can most easily be cut using a so-called backbiter instrument. These instruments have a cutting member which operates in a rearward manner, that is toward the proximal end of the instrument, and pivot to a closed position after backing into the tissue to be cut. Typically, these instruments look like either a reverse scissors or in one instance provide for a serrated moveable jaw member which punches or cuts the tissue into a cavity within the body of the instrument.

These instruments strive toward a low profile which enables them to be inserted through a smaller opening, while at the same time wanting to achieve the best cutting position and ease of use, while maintaining full control over the cutting or punching operation.

It is therefore an object of the invention to provide an improved backbiting medical instrument or punch which facilitates the cutting operation while maintaining a low profile, reliable operation, and ease of use.

SUMMARY OF THE INVENTION

The invention relates to a surgical cutting instrument for cutting body tissue and features an axially elongated support shaft, a ring-shaped jaw member having a through opening, the jaw member being mounted, preferably for support by the support shaft, for rearward pivotal movement at a pivot axis at a distal end of the elongated shaft for rearward movement toward and away from a closed cutting position. The opening lies in a plane generally parallel to the pivot axis. A fixed cutter, supported by the support shaft, is positioned in cutting alignment with the opening of the ring-shaped jaw member when it is brought to its closed position. The cutter is in a stationary position relative to the elongated support shaft and is located at a position between the pivot axis of the jaw member and a proximal end of the support shaft. The fixed cutter member and the ring-shaped member at its opening each have respective cooperative cutting edges which cooperate for cutting the body tissue when the jaw member pivots proximally to the closed position in which it cuttingly engages, aligns, and surrounds the fixed cutter member. An actuating member extends along the support shaft for causing opening and closing pivotable movement of the jaw member.

In specific embodiments of the invention, the fixed cutter has a serrated, parallel rib surface facing the jaw member as the jaw member closes. In particular, the fixed cutter has a blocking serration which extends parallel to the pivot axis, and which is that serration closest to the pivot axis. The blocking serration prevents tissue from blocking pivoting movement of the jaw member near the pivot axis. This serration extends so as to form a blocking partition even when the jaw member is in its fully opened position.

In another aspect, the invention features a jaw member which, at a end distance from the pivot axis, has a thickness in a direction normal to the plane of the opening which is less than the thickness, in the same direction, of the jaw member portion which surrounds the ring opening.

BRIEF DESCRIPTION OF THE DRAWINGS

Other objects, advantages, and features of the invention will be apparent from the following description taken together with the drawings in which:

FIG. 5 is a diagram showing the advantage of the smooth and thinned end section of the lower jaw member in accordance with a preferred embodiment of the invention.

DESCRIPTION OF THE PREFERRED EMBODIMENTS

Figure 1:
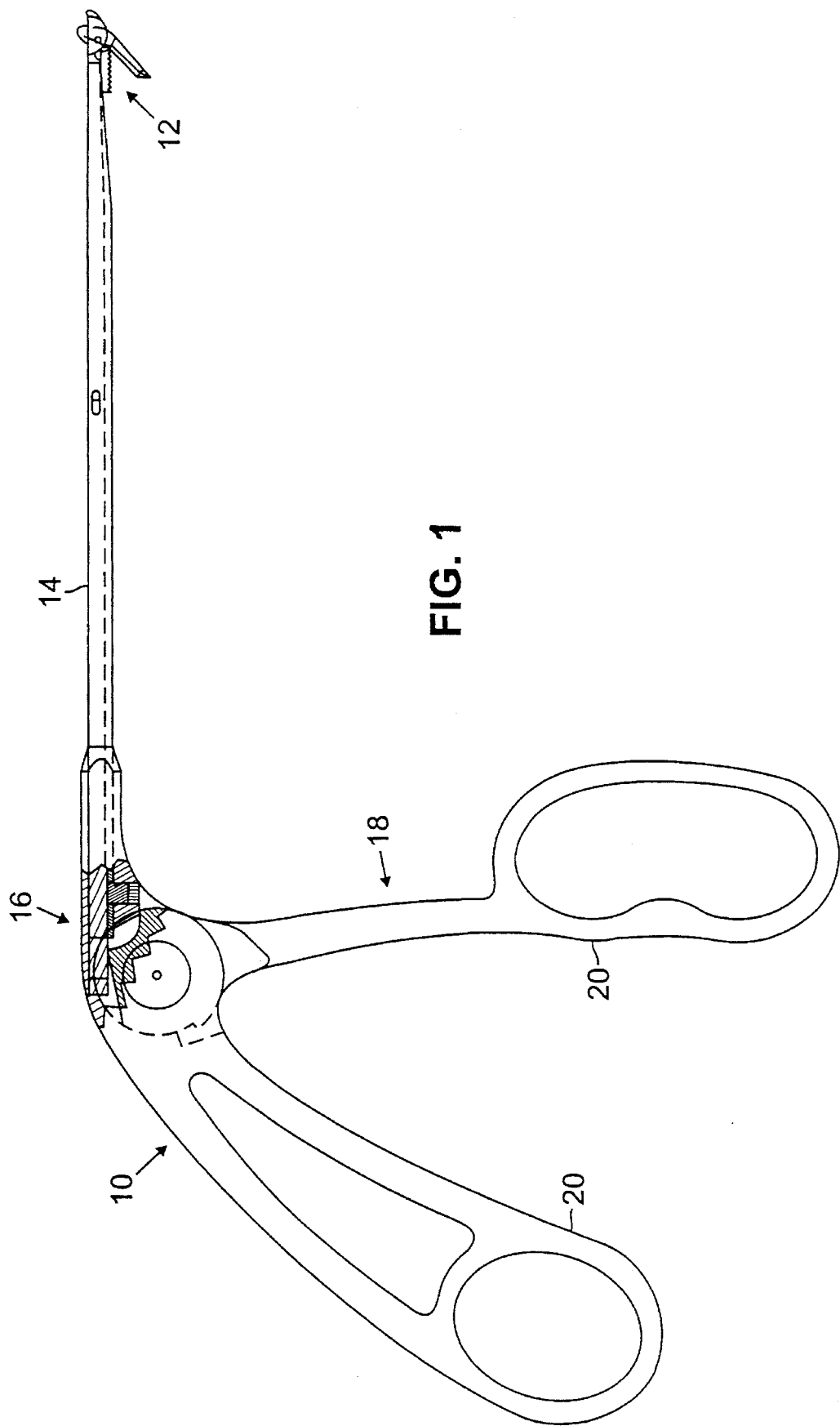
FIG. 1 is a overall view of the cutting instrument according to the invention.

Referring to FIG. 1, a medical surgical instrument 10 has a cutting distal end assembly 12 attached through an elongated support shaft 14 to an actuating mechanism 16 controlled by a handle assembly 18. The instrument 10, a so-called backbiter configuration, can be actuated by grasping end squeezing together the two finger grip members 20. As illustrated in FIG. 1, the cutter mechanism at the distal end is in its open position. This is illustrated in more detail in FIG. 2. In FIG. 3, the cutting mechanism is illustrated in a fully closed position.

Figure 2:
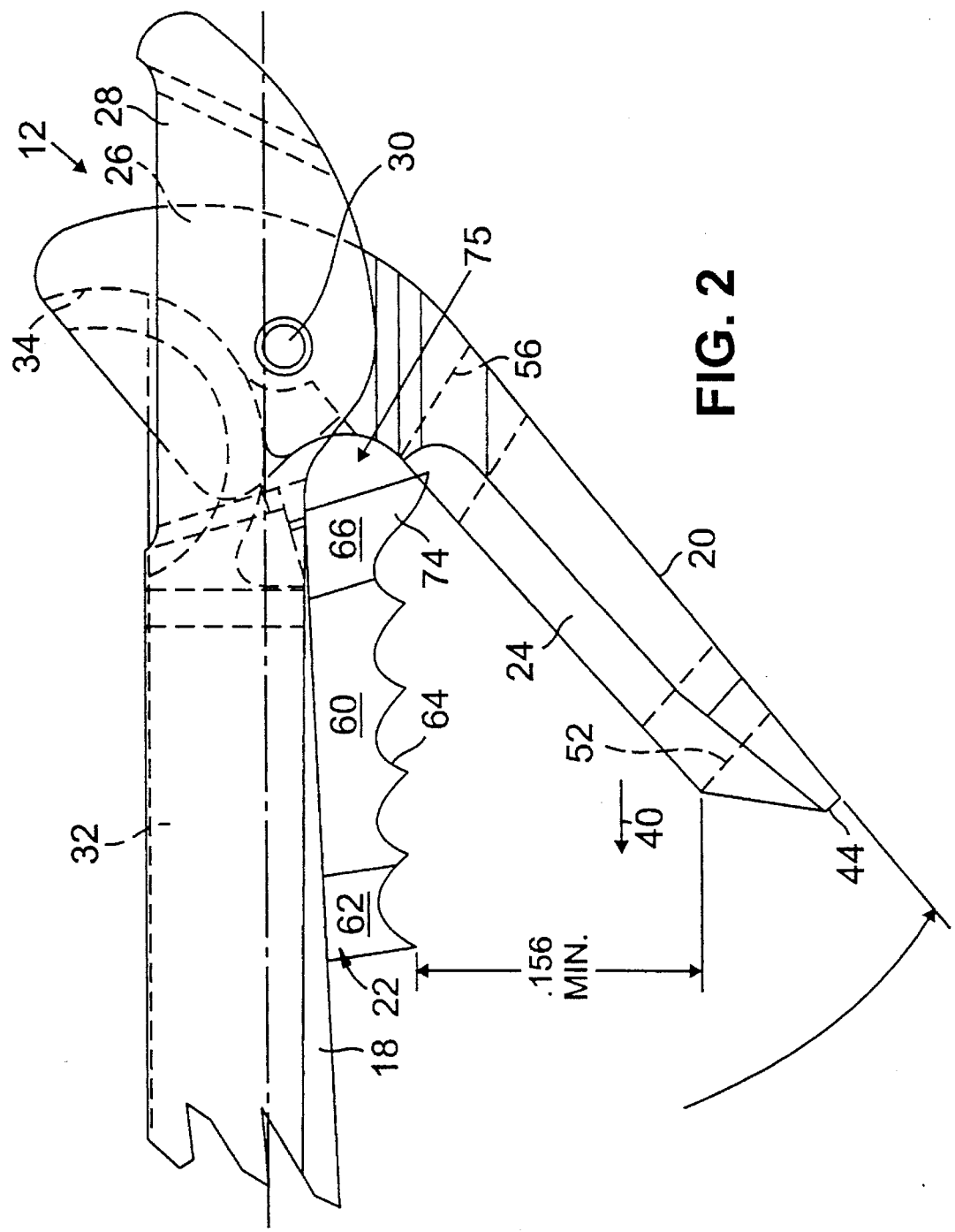
FIG. 2 is a detailed view of the cutting instrument with the jaw member in a fully open position.
Figure 3:
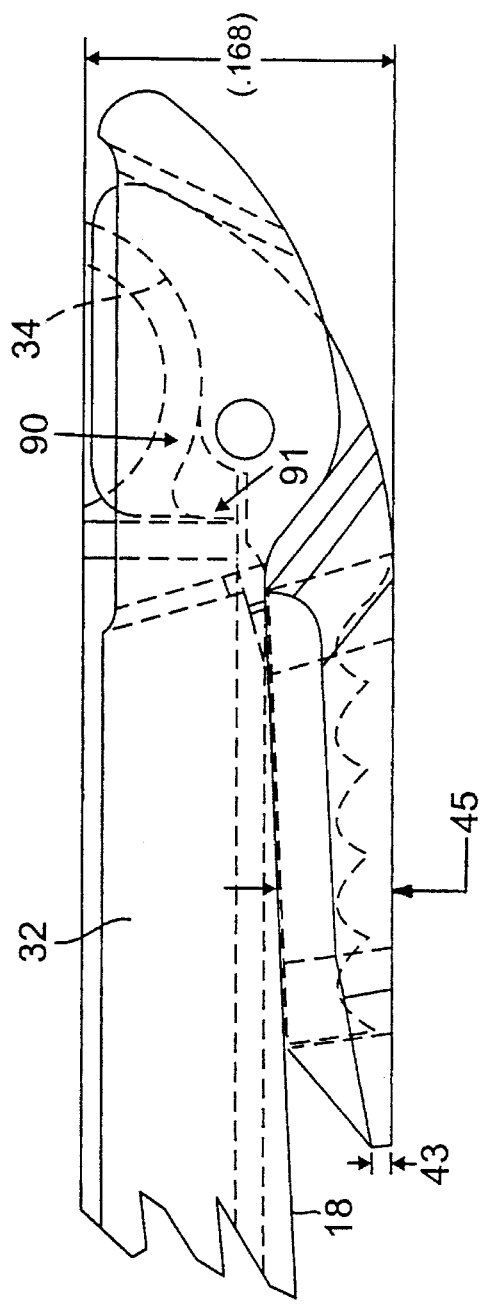
FIG. 3 is a detailed view of the cutting instrument with the jaw member in a fully closed position.
Figure 6:
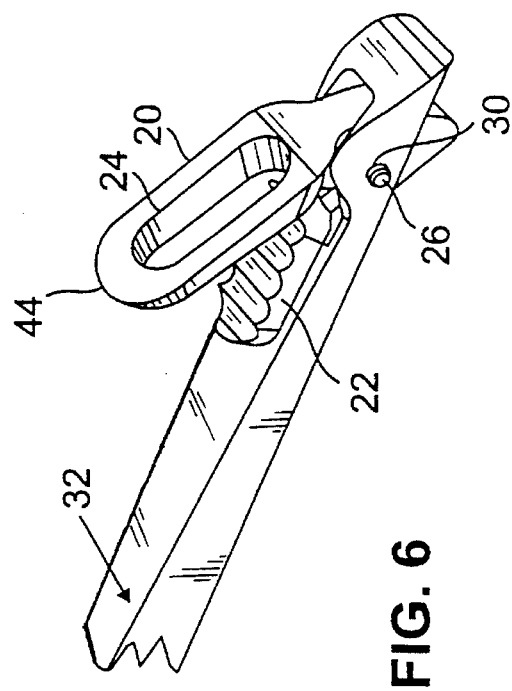
FIG. 6 is a detailed bottom view of the cutting members in an open position.

Referring to FIGS. 2 and 3, the cutting assembly 12 has a pivoting, ring-shaped lower movable jaw member 20 which cooperatively mates and aligns to a serrated fixed cutter member 22. Jaw member 20 and serrated member 22 cooperatively and cuttingly engaging in an aligned manner at opening 24 (see FIG. 3) in ring-shaped pivotable jaw member 20. The ring-shaped pivotable member pivots about a pivot axis 26. The pivoting member 20 is secured to the stationary elongated support shaft 14 at the pivot axis 26 by a pivot pin construction 30. The pivoting member 20 is moved from a fully opened position as shown in FIG. 2 to a fully closed position as illustrated in FIG. 3 by a slidable pushrod member 32 which engages, in a half-moon arrangement, the pivoting member along a surface generally designated as 34.

The pivoting ring-shaped lower jaw member 20 pivots rearwardly in a direction indicated by arrow 40 toward and away from its closed position wherein the opening 24 mates with and tightly but not interferringly encloses the serrated land cutting member 22. At an end 44 of jaw member 20 closest to the handle portion of the instrument, the ring-shaped member is tapered so that it has a thickness 43 at end 44 substantially less than the thickness 45 of the ring-shaped member at the opening 24. This reduced and smooth leading edge provides, as illustrated in FIG. 5, an advantageous ability to slide under and engage the meniscus for cutting or punching. When fully engaged within the instrument, the ring-shaped lower jaw member is pivoted to its fully closed position by which the tissue is cut or punched and thus becomes freely moveable, for removal at the surgical site, typically by suction as the site is continuously flushed with liquid.

Figure 4:
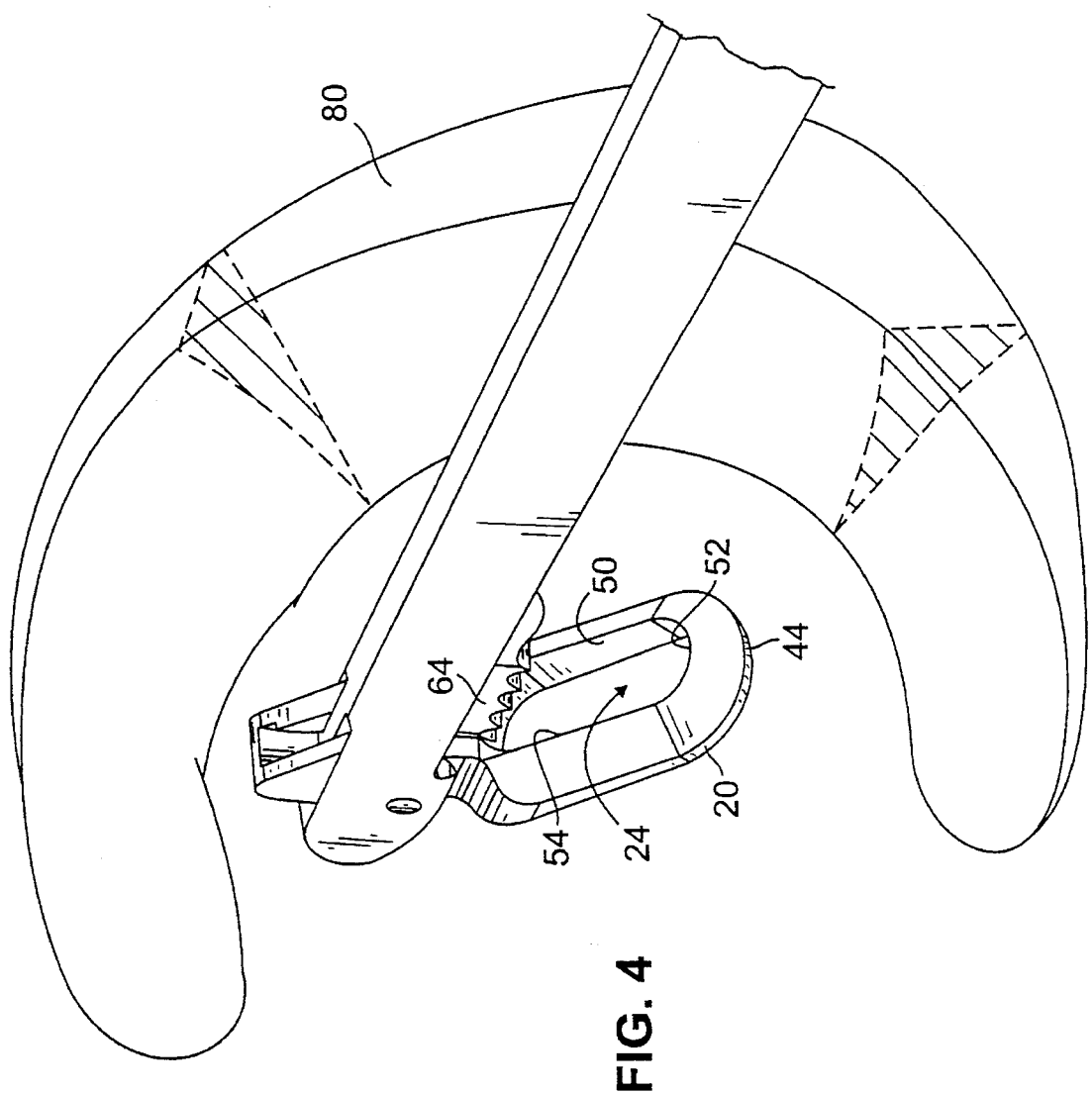
FIG. 4 is an operational view of the cutting instrument as it cuts a meniscus member.

The moveable ring-like jaw member has, referring to FIG. 4, sharp edges which form the cutting edges 50, 52, 54, 56 of opening 24, and which cooperate with corresponding cutting edges surfaces 60, 62, 64, 66 (FIG. 2) of the serrated fixed member 22. The action of closing ring-member 20 acts to cut or punch any tissue caught within the space defined by opening 24 of ring-member 20. Further, the serrations of fixed member 22, which extend parallel to each other and generally parallel to the pivot axis 26 about which the ring-like member rotates, tend to hold the tissue in place and to prevent it from slipping as the pivoting lower jaw member closes for cutting action. In particular, one of the serrations 74, is higher than the rest, in the illustrated embodiment, and acts to prevent tissue from moving behind the serrated land member into the space 75 at which the pivoting member rotates, so that it thereby prevents blocking and jamming of the rotation of the closed member during normal operation. Thus, serration 74 acts as a block to prevent tissue from moving into the distal end interior portion of the instrument support shaft.

Referring to FIG. 4, in operation, the medical instrument 10 with the lower ring like jaw member 20 in its fully opened position, can be used to engage a meniscus tissue which has a shape substantially as identified at 80 in FIG. 4. The thin forward leading edge 44 of lower jaw member 20 acts to more easily pick up and slide beneath the meniscus tissue, that is, between the meniscus and the tibial plateau, for example (FIG. 5). Once in place, the instrument is able to properly punch or cut the tissue, the punched or cut section being free to float at the surgical site and thereafter to be suctioned therefrom.

The actuation mechanism for causing the member 20 to pivot around pivot axis 26 is a pushrod arrangement having the pushrod 32, best identified in FIG. 3, which has at its distal end a moon or a semi-circular shaped actuating element 90. As this element moves forward (toward the distal end), as best shown in FIGS. 2 and 3, it engages surface 34 of jaw member 20 and causes that surface to move forward thus rotating about pivot axis 26 and urging the lower jaw member to its closed position. In this position, in the illustrated embodiment, the ring-shaped member fully encompasses the serrated fixed cutting member in a manner so that the serrations do not extend beyond the underside of the closed assembly. The assembly thus achieves a low vertical profile, with small lateral extent, and can be more easily removed (or inserted) through a smaller portal, for example, an anterior medial or anterior lateral portal. The actuating member 32 slides within the fixed shaft 14 of the medical instrument so that as it is withdrawn, that is pulled toward the end proximal to the handle, the half moon element of the slidable pushrod 32 acts against an extending surface 94 of the lower jaw member to cause the jaw member to pivot open as illustrated in FIGS. 2 and 3.

It is further important to note that both the sidewalls 62 and 66 of the fixed cutter member and 52 and 56 of the moveable lower jaw member are both angled slightly from a normal to their respective bases, to better allow the pivoting member to fit accurately, snugly, and without mechanical interference, in an aligned cutting relationship as the pivoting jaw member closes over and around the fixed serrated land member.

In other embodiments of the invention, the shape of opening 24, and hence the corresponding mating shape of fixed portion 22 can be altered as desired, and further the fixed portion 22 need not be serrated provided that its outer edges provide a cuttingly engaging interrelationship with corresponding edges of the ring-shaped member 20. Further, the size of the cutting instrument can be varied, depending upon the joint (for example, knee or wrist) and suction can be added if desired.

Additions, subtractions and other modifications of the claimed invention will be apparent to those of ordinary skill within the field and are within the scope of the following claims.

What is claimed is:

1. A surgical cutting instrument for cutting body tissue comprising an axially elongated support shaft, a ring-shaped jaw member having a through opening, said jaw member mounted for rearward pivotable movement at a pivot axis at a distal end of said jaw elongated shaft, said jaw member moving rearwardly toward and away from a closed cutting position, said opening lying in a plane substantially parallel to said pivot axis, a fixed cutter block, in cutting alignment with the opening of the ring-shaped jaw member in its closed position, said fixed cutter block being in a stationary position relative to the support shaft at a position between the pivot axis of said jaw member and a proximal end of said support shaft, said fixed cutter block and said ring-shaped member at the opening each having respective cooperative cutting edges which cooperate for cutting said body tissue when said jaw member pivots from said open position to said closed position in which said jaw member cuttingly engages, aligns with, and surrounds said fixed cutter block, and an actuating member extending along said support shaft for causing opening and closing pivotable movement of said jaw member.

2. The cutting instrument of claim 1 further wherein said fixed cutter block has a serrated, parallel rib, outer surface facing said jaw member as said jaw member closes.

3. The cutting instrument of claim 2 wherein said fixed cutter block has a blocking serration for preventing tissue from blocking pivoting movement of said jaw member near the pivot axis.

4. The cutting instrument of claim 1 wherein said jaw member, at an end distant from said pivot axis, has a thickness which is less than the thickness of the jaw member surrounding said opening.

5. The cutting instrument of claim 1 wherein said jaw member is mounted for support by said support shaft.

6. A surgical cutting instrument for cutting body tissue comprising an axially elongated support shaft, a ring-shaped jaw member having a through opening, said jaw member mounted for rearward pivotable movement at a pivot axis at a distal end of said elongated shaft, said member moving rearwardly toward and away from a closed cutting position, said opening, lying a plane substantially parallel to said pivot axis, and said jaw member, at an end distant from said pivot axis, having a thickness which is less than the thickness of the jaw member surrounding said opening, a fixed cutter block, in cutting alignment with the opening of the ring-shaped jaw member in its closed position, said fixed cutter block being in a stationary position relative to the support shaft at a position between the pivot axis of said jaw member and a proximal end of said support shaft and having, a serrated, parallel rib, outer surface facing said jaw member as said jaw member closes, said fixed cutting block and said ring-shaped member at the opening each having respective cooperative cutting edges which cooperated for cutting said body tissue when said jaw member pivots from said open position to said closed position in which said jaw member cuttingly engages, aligns with, and surrounds said fixed cutter block, said fixed cutter block having a blocking serration extending parallel to said pivot axis for preventing tissue from blocking pivoting movement of said jaw member near the pivot axis, and an actuating member extending along said support shaft for causing opening and closing pivotable movement of said jaw member.

* * * * *